United States Patent
Fischler

(10) Patent No.: US 9,615,900 B2
(45) Date of Patent: Apr. 11, 2017

(54) DEVICES FOR CONNECTING A DENTAL PROSTHETIC CONSTRUCTION TO A JAWBONE

(71) Applicant: VALOC AG, Mohlin (CH)

(72) Inventor: Titus Fischler, Zeiningen (CH)

(73) Assignee: VALOC AG, Mohlin (CH)

( * ) Notice: Subject to any disclaimer, the term of this patent is extended or adjusted under 35 U.S.C. 154(b) by 267 days.

(21) Appl. No.: 14/376,959

(22) PCT Filed: Feb. 6, 2013

(86) PCT No.: PCT/EP2013/052358
§ 371 (c)(1),
(2) Date: Oct. 10, 2014

(87) PCT Pub. No.: WO2013/117608
PCT Pub. Date: Aug. 15, 2013

(65) Prior Publication Data
US 2015/0297322 A1  Oct. 22, 2015

(30) Foreign Application Priority Data

Feb. 7, 2012 (EP) .................................... 12154311
Sep. 21, 2012 (EP) .................................... 12185561

(51) Int. Cl.
*A61C 8/00* (2006.01)
*A61C 13/265* (2006.01)
*A61C 5/08* (2006.01)

(52) U.S. Cl.
CPC .............. *A61C 8/0062* (2013.01); *A61C 5/08* (2013.01); *A61C 8/0068* (2013.01); *A61C 8/0089* (2013.01); *A61C 13/2656* (2013.01)

(58) Field of Classification Search
CPC ..... A61C 8/0012; A61C 8/0048; A61C 8/005; A61C 8/0062; A61C 8/0089; A61C 8/0068; A61C 13/2656; A61C 5/08
See application file for complete search history.

(56) References Cited

U.S. PATENT DOCUMENTS 5,480,304 A    1/1996  Nardi
5,997,298 A *  12/1999 Nowak .............. A61B 17/1604
                                                    433/165

(Continued)

FOREIGN PATENT DOCUMENTS

| DE | 92 02 656.7 U1 | 4/1992 |
| EP | 0 891 750 A1 | 1/1999 |
| EP | 2 266 498 A1 | 12/2010 |

OTHER PUBLICATIONS

International Search Report for International Application No. PCT/EP2013/052358 dated Jun. 6, 2013.

*Primary Examiner* — Glenn Richman
(74) *Attorney, Agent, or Firm* — Kratz, Quintos & Hanson, LLP

(57) ABSTRACT

A male piece for reversible and detachable connection of a dental prosthetic construction to a jawbone, said male piece being designed with a fastening structure, by means of which the male piece can be fastened onto the jawbone, onto an implant that has been implanted in the jawbone, onto a tooth stump or onto a neighboring tooth, comprising a body section having an exterior surface corresponding to a lateral surface of a cylinder, such that the central axis of the cylinder defines a longitudinal axis of the male piece; a snap-on section, which is offset axially with respect to the longitudinal axis of the male piece relative to the body section, said snap-on section, comprising an exterior surface with a convex curvature along the longitudinal axis, which protrudes outward from the longitudinal axis of the male (Continued)

piece beyond the exterior surface of the body section; and a head end, which terminates the male piece axially with respect to its longitudinal axis, wherein the snap-on section is arranged closer to the head end than is the body section, and a concave intermediate section is arranged between and the head end and the convexly curved exterior surface of the snap-on section.

12 Claims, 5 Drawing Sheets

(56) References Cited

U.S. PATENT DOCUMENTS

| | | | |
|---|---|---|---|
| 8,057,230 B1* | 11/2011 | Folsom, Jr. | A61C 8/0012 |
| | | | 433/174 |
| 8,784,103 B2* | 7/2014 | Studer | A61C 8/005 |
| | | | 433/172 |
| 2004/0005530 A1 | 1/2004 | Mullaly | |
| 2005/0019730 A1 | 1/2005 | Gittleman | |
| 2005/0250072 A1* | 11/2005 | Laux | A61C 8/0048 |
| | | | 433/169 |
| 2010/0055645 A1 | 3/2010 | Mullaly | |

\* cited by examiner

DEVICES FOR CONNECTING A DENTAL PROSTHETIC CONSTRUCTION TO A JAWBONE

TECHNICAL FIELD

The invention relates to a male piece and an abutment with such a male piece, a retention insert for snapping onto such a male piece and the corresponding connecting device. Such a male piece being designed with a fastening structure, by means of which the male piece can be fastened onto the jawbone, onto an implant that has been implanted in a jawbone, onto a tooth stump or onto a neighboring tooth, and which defines a body section having an exterior surface that corresponds essentially to the lateral surface of a cylinder, wherein the central axis of the cylinder defines a longitudinal axis of the male piece, which comprises a snap-on section that is offset axially toward the body section with respect to the longitudinal axis of the male piece and comprises an exterior surface with a convex curvature protruding beyond the exterior surface of the body section from the longitudinal axis of the male piece outward and a head end, which terminates the male piece axially with respect to its longitudinal axis, wherein the snap-on section is arranged to be closer to the head end than the body section, can be used for reversibly detachable connection of a dental prosthetic construction to the jawbone.

PRIOR ART

In dental medicine today, damaged or diseased teeth are routinely replaced by an artificial tooth or denture. Implants are frequently implanted as a dental root replacement into a jawbone of a patient such that an abutment is placed on the implant in certain embodiments. The implant or the abutment is thus designed on its longitudinal end which faces away from the jawbone, i.e., on its occlusal end with a connecting structure on which a prosthetic construction can be detachably mounted.

In a popular embodiment, this connection between the abutment and the prosthetic structure is designed as a pushbutton connection, where typically a male part of the pushbutton connection, i.e., the male piece is formed on the abutment and/or on the implant and the female part of the pushbutton connection, i.e., the female piece, is connected to the prosthetic construction. With such pushbutton systems, the prosthetic construction can easily be snapped on to the respective implants and/or abutments and can also be released from them again.

WO 2010/025034 A1, for example, describes a dental anchoring device, which comprises a male piece head, which is formed on the abutment or directly on the implant, as well as a female housing, which is fixedly connected to the prosthetic construction. The female piece additionally comprises a retention insert which is inserted into the female housing before the female piece together with the prosthetic construction is snapped onto the male head. The male head has a flat head end and a convex exterior surface of the snap-on surface that is curved an opening with an inside profile in the male head is formed in the flat head end, so that, on the one hand, a screwdriver can be used for screwing the abutment and/or the implant and, on the other hand, a punch and/or a plug can be used for the retention insert.

Another pushbutton connection system is described in WO 2011/027229 A2, where the female piece is refined in particular, so that the retention insert is securely connected to the female piece housing by means of a locking mechanism when the female piece snapped onto the male piece.

Since the retention inserts with these pushbutton systems can be tilted only within a limited angular range on the male piece, one disadvantage may be the fact that prosthetic structures snapped onto the male piece can be tilted accordingly only to a limited extent on the male piece. Frequently, however, when using pushbutton systems an improved tiltability of the prosthetic construction is desired.

Improved properties in this regard are typically offered by pushbutton systems having spherical male pieces. For example, U.S. Pat. No. 5,211,561 A describes on such pushbutton system which has a male piece having a spherical head. However, such spherical male heads can pose considerable problems in secure fastening of the female piece and/or the female piece housing to the prosthetic construction.

In this process, retention inserts with a respective female housing are typically first placed on the male pieces of implants and/or abutments that have already been implanted. Next the prosthetic construction is placed on the female piece housing in such a way that the housing sits in a recess in the prosthetic construction where it is then fixedly connected to the prosthetic construction, for example, by polymerization of the recess.

However, due to the relatively good and/or easy tiltability of the retention inserts and the female housing on the male piece and/or due to the relatively unstable arrangement of the retention inserts and the female piece housing on the spherical male pieces, it is difficult to be sure during the connection of the female housing to the prosthetic construction that the retention inserts and the female housing are all arranged exactly axially on the male piece. In many cases, this cannot be adequately ensured, which may result in the female housing being connected to the prosthetic construction with a slight tilt and/or inclination with respect to the male piece, so that the prosthetic construction can then no longer be snapped onto the implant optimally and/or with optimal clearance for movement.

The object of the following invention is therefore to propose a construction which, on the one hand, permits a relatively good tiltability of the female piece(s) of a prosthetic construction and, on the other hand, permits a relatively accurate positioning of the female piece(s) on the corresponding male pieces and thus an accurate production of the prosthetic construction as intended in a relatively simple and efficient manner.

DESCRIPTION OF THE INVENTION

This object is achieved according to the invention by a male piece as defined in the following as well as by advantageous embodiments defined hereinbelow.

The gist of the invention is as follows: a male piece for reversibly and detachably connecting a dental prosthetic construction to a jawbone is designed with a fastening structure, by means of which the male piece can be secured on a tooth stump or on a neighboring tooth in the jawbone, on an implant which is implanted in the jawbone, and this male piece comprises a body section with an exterior surface that corresponds to a lateral surface of a cylinder, such that the central axis of the cylinder and/or of the body section defines a longitudinal axis of the male piece. The male piece also comprises a snap-on section, which is axially offset with respect to the longitudinal axis of the male piece relative to the body section, and which has an exterior surface having a convex curvature along the longitudinal axis, said exterior surface protruding distally, i.e., toward the outside, beyond the exterior surface of the body section outward from the longitudinal axis of the male piece. In addition, the male piece comprises a head end, which forms an axial finish on the male piece with respect to its longitudinal axis. Within the male piece according to the invention, the snap-on section is arranged closer to the head end than the body section, and a concave intermediate section is arranged between the head end and the convexly curved exterior surface of the snap-on section.

The term "male piece" in the sense of the present invention may be understood to refer to an apparatus that is attached to the jawbone during use and can be mounted on and dismounted from a female piece which is permanently attached to a prosthetic construction. The male piece can therefore make available a male part of a connecting structure that resembles a pushbutton. For example, the male piece may be designed as a one-piece implant having a fastening structure with an outside thread by means of which the implant can be screwed into the jawbone and implanted there, as an abutment with a fastening structure which is designed to fit a corresponding structure of a implant for mounting on the implant, as an abutment cover for attachment to an abutment, as a bridge construction, as a dental root pin or as a cap for a tooth stump. The male piece may also be part of one of the devices mentioned above or a similar device. The term "reversibly detachable connection" in the context of the male piece may be understood to refer to a connection for mounting or for insertion of a prosthetic construction in a patient's mouth. The connection should be reversible, so that it can be detached repeatedly, so the prosthetic construction can be inserted and then removed again. In particular, this can be implemented by means of a pushbutton connection, in which the prosthetic construction is snapped onto the male piece for insertion and is then removed again for removal therefrom.

In conjunction with the invention, the term "convex" with respect to the male piece and/or parts thereof can be understood to refer to shapes having an outward curvature, an outward bend, an outward bulge, an outward upset or the like. The term "having a convex curvature along the longitudinal axis" with respect to the exterior surface of the snap-on section, refers to a curvature in the direction of the longitudinal axis, i.e., a curvature in a sectional plane comprising the longitudinal axis. Similar to that and in the same context, the term "concave" with respect to the male piece and/or parts thereof that have been mentioned may be understood to refer to shapes having an inward curvature, an inward bend, an inward bulge, an inward inversion or the like.

In some embodiments the exterior surface of the snap-on section may have a convex curvature completely along the longitudinal axis. In other embodiments the exterior surface of the snap-on section may have a plurality of convex regions along the longitudinal axis, these convex regions being joined to one another by means of regions having no curvature or no convex curvature. For example, the snap-on section may have two regions with a convex curvature with an axial distance between them along the longitudinal axis and connected to one another by means of a region with a concave curvature along the longitudinal axis. The "snap-on section" may be understood to refer to the section of the male piece which comprises all the regions of the male piece by means of which a female piece may be held on the male piece.

The intermediate section of the male piece according to the invention may be arranged between the snap-on section and the head end, in such a way that no region is left between the intermediate section and the head end, over which a male piece and/or the prosthetic construction can be held and/or onto which it can be snapped, in particular no additional snap-on section. The intermediate section preferably passes over directly into the head end. It may also pass over directly into the snap-on section.

The term "prosthetic construction" is understood in the context of the present invention to refer to various constructions that are suitable, depending on the use, such as those known, for example, as individual, partial or complete dentures, bridges, crowns, hybrid or complete prostheses.

The male piece and in particular its head end, its snap-on section and its intermediate section may also be designed to be essentially rotationally symmetrical. Depending on the design and the area of use, they also may be manufactured from suitable materials accordingly, wherein, for example, titanium, zirconium oxide, polyaryl ether ketones (PAEK), polyether ether ketones (PEEK), polyether ketone ketone (PEKK) or modifications thereof that have been optimized for medical applications may be used. Such a male piece may typically fulfill the purpose of ensuring an accurately fitting attachment to the patient's jawbone on the one hand, while on the other hand making available means by which the prosthetic construction can be secured reliably.

The snap-on section of the male piece according to the invention makes it possible to provide a releasable pushbutton connection between the male piece and the prosthetic construction.

In use of the male piece according to the invention, in the production of a prosthetic construction the male piece and/or a plurality of such male pieces may be connected to a jawbone. This may be accomplished by means of a direct connection to the jawbone or by means of an indirect connection to the jawbone, depending on the design of the male piece, for example, as an abutment over an implant, as an abutment cover over an abutment and an implant or over a tooth stump.

In parallel with this, the prosthetic construction may be prepared in such a way that openings and/or blind holds or recesses are provided in the location(s) of the prosthetic construction where the prosthetic construction is to be connectable to the male piece(s) by means of one or more female pieces. Then retention inserts and a suitable female housing may be placed on the male pieces. In doing so, the geometry of the male pieces according to the invention, in particular with their concave intermediate sections allows the retention inserts to be suitably held on the male pieces in a predetermined orientation and to prevent unintended tilting of the retention inserts on the male pieces. The male piece according to the invention can exert an intrinsic centering function on the female piece and/or its retention insert due to the design of its head. In particular due to the shape of the head of the male piece, the retention insert can be put under a slight prestress if tilted so that it is automatically moved back into the aforementioned preferred predetermined alignment and/or position as soon as it has the required clearance to do so. In this preferred predetermined alignment and/or position, the male pieces may then we arranged in the openings in the prosthetic construction and the female piece housing may be securely connected to the prosthetic construction, for example, by fully polymerizing the openings.

In daily use of the male piece according to the invention and/or the prosthetic construction that can be connected to it—as described below in detail in a preferred embodiment—the head end of the male piece may be designed so that, together with the snap-on section, it allows relatively great tilting of the female piece on the male piece, which may be desirable and/or comfortable in various regards. The shape of its head end also allows the female piece that is mounted on the prosthetic construction to be accurately positioned in a simple and relatively gentle manner when placed on the head, so that comfortable use of the prosthetic construction is possible and damage to the female piece due to corners or edges of the head end can be prevented.

The design of the male piece according to the invention also allows the head end to be arranged at a relatively great axial distance from the end of the snap-on section opposite the body section. Therefore, the head end of the male piece may be situated at a higher level in comparison with its snap-on section, i.e., it extends further into the interior of the mouth than the snap-on section. The head end may be further elevated from the gingiva in this way in comparison with the snap-on section, so that the male piece can be localized relatively easily and unambiguously before inserting the prosthetic construction. As will also be shown in greater detail below in a preferred embodiment, it is possible to prevent the superstructure from being inappropriately tall due to a design of the other components of the superstructure having been adapted at the same time, in particular the retention insert.

Thus, the geometry of the male piece according to the invention makes is possible for the female piece to be easily held and/or centered in a starting position and/or in a predetermined alignment and position, on the one hand, so that the prosthetic construction can be provided in a precise and intended orientation with the female piece in a relatively simple manner. On the other hand, the male piece also allows the prosthetic construction to be tiltable to a relatively great extent without causing the male piece to snap out of the female piece, which may be important in particular in the case of prosthetic constructions attached to the jawbone by means of two male pieces only. Furthermore, the prosthetic construction may also be inserted relatively easily and efficiently into a patient's mouth by means of the male piece according to the invention.

The intermediate section of the male piece according to the invention preferably has an exterior surface with a concave curvature. Such a design of the male piece permits a preferred and sufficiently easy holding of the female piece in a predetermined alignment and/or position. Furthermore, the exterior surface with this curvature permits a gentle and convenient centering and placement of a female piece.

The head end of the male piece is preferably completely closed and has a completely convex curvature. In this context, the term "closed" indicates that the surface of the head end does not have any openings, which are not due to properties of the material used such as its porosity. In particular this is understood to mean that the head end does not have any opening for insertion of a tool or a retention stopper or for a similar purpose. Such a design of the head end makes it possible for attachment of a fitting female piece and in particular its retention insert to take place relatively easily. In particular the female piece can be centered and positioned over the curvature of the head end in such a way that the female piece slides along the curvature until it is centered on the male piece and/or on the snap-on section of the abutment, so that slight pressure and snapping of the female piece onto the snap-on section of the male piece are possible. Damage to the female piece can then also be prevented due to the curved shape of the head end. Furthermore, such a closed design of the head end permits an improvement in hygiene because it is impossible for food residues or other contaminants to become trapped in openings.

The head end of the abutment preferably corresponds essentially to a segment of a spherical surface. Thus the head end can preferably be designed with a convex curvature in a relatively simple manner.

The segment of the spherical surface of the head end preferably has a first radius of curvature and the convexly curved exterior surface of the snap-on section has a second radius of curvature, such that the first radius of curvature is larger than the second radius of curvature. On the one hand, such a design of the male piece permits an efficient and expedient snapping of a female piece onto the snap-on section, so that the female piece can be held adequately on the male piece. On the other hand, the softer roundness of the head end allows the female piece to be tiltable on the male piece to a relatively great extent without unsnapping it. In a preferred embodiment, the first radius of curvature is approximately two to approximately four times as large as the second radius of curvature and in particular is approximately three times as large. The term "approximately" in conjunction with the size ratios of the first radius of curvature and of the second radius of curvature may relate to a value which is within 20%, within 10%, within 5% or within 2% of the given value. Furthermore, the term "approximately" may relate precisely to the value given in particular.

Another aspect of the invention relates to an abutment for connection of a dental prosthetic construction to a jawbone as an embodiment of the male piece according to the invention. The abutment comprises a male piece as described above and a fastening structure by means of which the abutment can be fastened onto the jawbone or onto an implant that is implanted in the jawbone. The term "abutment" is understood in conjunction with the present invention to refer to a connecting structure and/or a connecting piece and/or a post having means by which a prosthetic structure can be attached so that with the intended use of the abutment, the prosthetic construction can be mounted on the jawbone in a patient's mouth. Such abutments as a one-piece structure may be provided with an implant body by means of which it can be connected directly to the patient's jawbone. For example, the implant body may have an outside thread as a fastening structure by means of which the abutment can be screwed into the jawbone and implanted there. As an alternative to this, the abutment may also be designed to be attached to a separate implant, so that the implant and abutment are designed in two parts. The fastening structure of the abutment is preferably designed to fit with a corresponding structure of the implant, so that it can be efficiently connected thereto. The fastening structure may be designed suitably in a known way. Typically such an abutment may, on the one hand, fulfill the purpose of ensuring an accurately fitting connection to an implant that is implanted in the patient's jawbone, while, on the other hand, making available means to which the prosthetic construction can be securely attached.

The parts of the total prosthetic and implant device which protrude beyond the gingiva and/or the drums into the oral cavity during use and are thus visible from the outside can be referred to as "superstructure." For example, the superstructure may comprise the prosthetic construction, a connecting device (female piece) comprising a housing and a retention insert as well as, in particular in the two-part embodiment of the abutment mentioned above, the abutment itself or at least parts thereof as well as its male piece.

In certain embodiments of the abutment, the body section of the male piece may also be designed with a bend and/or a kink. In such a case its exterior surface corresponds essentially to the lateral surface of a curved or bent cylinder wherein the central axis of this curved or bent circular cylinder defines the longitudinal axis of the abutment on its end facing the head end of the abutment.

The design of the abutment according to the invention makes it possible for the effects and advantages mentioned above in conjunction with the male piece to be implemented with the abutment.

The fastening structure of the abutment preferably has a screw section extending away from the head end of the male piece having an outside thread formed at least partially on said screw section. Such a fastening structure makes it possible for the abutment to be screwed onto a corresponding inside thread of an implant for fastening purposes, for example. The fastening structure may also be designed with the screw section having an outside thread so that it can be screwed directly into a jawbone. A suitable screwdriver may be used to screw it in. Such an outside thread thus permits a simple and efficient means of fastening the abutment.

The fastening structure preferably comprises a wrench attachment section arranged between the screw section and the male piece. The wrench attachment section may be designed as a cylinder whose lateral surface has a cross section embodied essentially as a polygon. In this way or in some other way, the wrench attachment section may preferably be designed to be cylindrical such that preferably four, five, six or eight planar acting surfaces are provided on the lateral surface and disposed along the circumference of the lateral surface. The essentially rectangular acting surfaces of the exterior surface of the wrench attachment section, for example, permit the abutment to be gripped from the outside for screwing it or unscrewing it. This may be accomplished in particular by a specifically adapted screwdriver, as mentioned above. The above-mentioned cross section of the cylinder of the lateral surface may be essentially in the form of a square, a hexagon or an octagon. Such an embodiment as a square, hexagonal or octagonal cylinder permits a relatively simple arrangement, so that it is possible to ensure that the acting surfaces are designed so that suitable forces can be transferred to the abutment by means thereof for screwing the abutment.

The abutment may comprise an essentially cylindrical gingival height section which protrudes outward from a longitudinal axis of the abutment beyond the male piece. With such a gingival height section, the height of the abutment may be adjusted so that the male piece is situated essentially above the gingiva so that it is accessible from the oral cavity when the abutment is connected to the jawbone. The height of the gingival height section may be in a range from approximately 0.5 mm to approximately 8 mm, preferably in a range from approximately 1 mm to 6 mm and in particular in a range from 1.5 mm to 5.5 mm.

The gingival height section can protrude outward from the longitudinal axis of the abutment beyond the screw section of the fastening structure such that a stop may be provided between the gingival height section and the screw section of the fastening structure. Such a stop makes it possible for the abutment to lie in flush contact with a respective implant when it is connected thereto. For example, a relatively uniform wide area transfer of force from the abutment to the implant and in the opposite direction as well can be achieved in this way. The stop here is preferably designed as an essentially planar surface arranged essentially at a right angle to the longitudinal axis between the body section and the screw section of the fastening structure.

The screw section of the fastening structure of the abutment may have an intermediate section without an outside thread and a threaded section with an outside thread. Then the intermediate section of the screw section of the fastening structure may taper from the gingival height section to the threaded section. The intermediate section may have at least one step. The steps with which the intermediate section is also tapered may be designed to be angular, curved, parabolic or the like. Forces which act along the longitudinal axis of the abutment can be transferred to a respective implant at several locations, for example, with such steps in the longitudinal direction of the abutment. Thus, for example, in the case of application of a force and/or in a biting motion, an advantageous distribution of force to the abutment and/or the implant can be achieved. Furthermore, such steps may also be helpful in fastening the abutment, for example, for a distribution of forces.

A maximum cross section of the snap-on section of the male piece perpendicular to the longitudinal axis of the abutment may have a diameter from approximately 2.1 mm to approximately 2.7 mm and in particular approximately 2.3 mm. A snap-on section having such dimensions permits a relatively small pushbutton connection, which may permit an increased flexibility and improved comfort with many prosthetic constructions and/or applications. For comparison purposes, corresponding diameters of traditional pushbutton connections are in a range from approximately 3.8 mm to approximately 4 mm. According to these dimensions of the snap-on section of the abutment, the diameter may thus be reduced by approximately 30% to approximately 40%. In particular together with a retention insert according to the invention, despite the preferably smaller dimensions of the snap-on section, adequate holding forces and/or pull-off forces and/or retention forces may be ensured. Furthermore, the preferred design of the head end of the abutment with a convex curvature permits a simple and clean attachment of the prosthetic construction to the abutment, even when such snap-on sections are relatively small.

Another aspect of the present invention relates to a retention insert for snapping onto a snap-on section of a male piece, as described above. The retention insert has an end side and an at least partially ring-shaped retention edge protruding away from that, such that the end side and the retention edge protruding away from it form a frame, which encloses a first concave region, which is designed to correspond to the exterior surface of the snap-on section of the male piece, a second region, which is designed to receive the head end of the male piece, and a third region, which is designed between the first region and the second region. In conjunction with the retention insert, the term "concave" with respect to the body of the retention insert and/or the aforementioned parts thereof may be understood to refer to the same curving inwardly, bending inwardly, bulging inwardly, upended inwardly or similar designs.

Such a retention insert allows universal use with a male piece according to the invention and/or with an abutment according to the invention as well as with a known male piece having an opening on its head end and/or a flat or planar head end. It is thus possible for various types of male pieces and/or abutments to be cared for with a type of retention insert in parallel, which may facilitate work for the general practitioner or for an orthodontist. In particular, the third region of the retention insert facilitates bracing and/or support on such a traditional male piece. The second region of the frame of the retention insert may remain empty here.

In use of the retention insert together with a male piece and/or an abutment as described above, the first, second and third regions also allow a female piece, which encloses the retention insert, to be tiltable to a preferred extent on the male piece without releasing the female piece from the male piece. At the same time, the retention insert allows the insert to be prestressed in tilting on the female piece, so that it is moved automatically back into its untilted starting position and/or initial placement when no external tilting force is acting on it. This makes it possible to implement an intrinsic centering function, which may facilitate the production of a prosthetic construction, as described above. To prestress the retention insert, it may be elastically deformed and/or bent, for example.

The second region of the frame of the retention insert is preferably designed as a continuous opening in the end. The opening may have a round cross section, i.e., a circular cross section in particular. Such a second region permits a relatively simple efficient design of the retention insert according to the invention.

The third region of the frame preferably has a conical interior surface, which tapers from the first region of the frame to the second region of the frame. Such a third region allows efficient production of the retention insert and allows the desired advantageous effect also with respect to prestressability.

The retention edge preferably has an extension region, which is connected to the first region of the frame opposite the third region of the frame. The extension region here may have in particular an inside, which corresponds essentially to the inside of the ring and is designed to be planar. Such an extension region makes it possible for the retention insert to be tiltable on a male piece to an increased extent. In particular the corresponding advantageous effect of the male piece and/or of the abutment can be supported and improved in this way. The retention insert here preferably includes a longitudinal central axis wherein a diameter of a maximum cross section of the first region arranged perpendicular to the central longitudinal axis has a length of between approximately six and approximately fourteen times the thickness of the extension region, preferably between approximately eight and approximately twelve times and in particular approximately ten times the thickness.

The term "approximately" in conjunction with the length of the diameter of the cross section of the first region may relate to a value and/or a range which is within 20%, within 10%, within 5% or within 2% of the given value and/or range. Furthermore, the term "approximately" may also relate precisely to the stated value and/or range in particular. The term "essentially perpendicular" with respect to the arrangement of the cross section of the first region relative to the central axis will relate to an angle value which is within 20%, within 10%, within 5% or within 2% of the stated value of 90°. It may also relate to an angle of 90° in particular in a precisely perpendicular design. With these ratios of the first region and of the extension region, an efficient and expedient embodiment of the retention insert according to the invention may preferably be implemented.

Another further aspect of the present invention relates to a connecting device which comprises a male piece as described above and a retention insert as described above. The third region of the retention insert is arranged at least partially at a distance from the intermediate section of the male piece when the retention insert is snapped onto the male piece and no external force acts on the retention insert and/or on the male piece. The term "external force" in this context can be understood to refer to a force that acts from the outside and moves the retention insert onto the male piece, for example. A force acting between the retention insert and the male piece to hold the retention insert on the male piece cannot be understood to be a force in the aforementioned sense in particular. Such a connecting device makes it possible for the self-centering function, which is described in detail above according to the invention, to be implementable in a relatively efficient manner, while at the same time, permitting the preferred tilting possibility described above. Among other things, the distance between the intermediate section of the male piece and the third region of the retention insert can allow the retention insert to be elastically bent and thus to be prestressed when it is placed on the male piece. Furthermore, such a combination of the male piece according to the invention with the retention insert according to the invention makes it possible to design the snap-on section of the male piece to be relatively small in dimension and nevertheless to provide adequate retention forces.

The retention insert described above as well as the retention insert of the connecting device can be further refined as described below:

The retention insert may be designed so that it can be arranged in a receptacle in the holding shell formed by a holding edge and an end side of a holding shell and/or a female piece housing, such that an exterior surface of the retention edge of the retention insert is adjacent to an internal surface of the holding edge of the holding shell.

The retention insert is preferably designed so that the exterior surface of the retention edge of the retention insert is arranged at least partially at a distance from but near the interior surface of the holding edge of the holding shell, when the retention insert is arranged in the receptacle of the holding shell, and when essentially no radial forces are acting on the holding edge of the holding shell and on the retention edge of the retention insert.

The retention insert may be designed so that the exterior surface of the retention edge of the retention insert is arranged at least partially at a distance from but near the interior surface of the holding edge of the holding shell in that the exterior surface of the retention edge of the retention insert is inclined more in the direction of a central axis of the connecting device than the interior surface of the holding edge of the holding shell.

The retention edge may have a projection which extends radially from the exterior surface of the retention edge such that the projection is designed according to a groove extending from the interior surface of the holding edge of the holding shell. The projection of the retention edge can be arranged in the groove of the holding edge of the holding shell in such a way that the retention insert is releasably held in the holding shell when the retention insert is arranged in the receptacle of the holding shell and when essentially no radial forces are acting on the holding the edge of the holding shell or on the retention edge of the retention insert. The projection of the retention edge of the retention insert may comprise an essentially planar projection support surface such that a part of the projection support surface is in contact with a part of an essentially planar groove support surface of the groove of the holding edge of the holding shell when the retention insert is arranged in the receptacle of the holding shell and when essentially no radial forces are acting on the holding edge of the holding shell and on the retention edge of the retention insert and such that the projection support surface is designed to be rounded toward its end facing the holding shell.

The projection of the retention edge may be designed so that it can be disposed in the groove of the holding edge of the holding shell in such a way that the retention insert is permanently connected to the holding shell when the retention insert is arranged in the receptacle of the holding shell and when a radial force acts on the retention edge of the retention insert in the direction of the holding edge of the holding shell and/or on the holding edge of the holding shell in the direction of the retention edge of the retention insert.

The retention edge of the retention insert may have an interior surface opposite the exterior surface such that the interior surface is designed to be rounded toward the end facing away from the end of the retention insert. The retention insert may be made of a biocompatible polymer material, in particular a polyether ether ketone.

Another aspect of the present disclosure relates to a method for connecting a dental prosthetic construction to a jawbone. This method comprises: fastening an abutment as described above, such that the abutment has a fastening structure by means of which the abutment is fastened onto the jawbone, on an implant which is implanted in the jawbone, on a tooth stump or on a neighboring tooth; securely mounting a holding shell on the prosthetic construction; axial impression of a retention insert as described above into the holding shell until the retention insert is disposed in the holding shell; disposing the prosthetic construction on the abutment so that a head end of the abutment is in contact with the retention insert; and pressing the prosthetic construction onto the abutment so that the retention insert is pressed axially over a snap-on section of the abutment and then is snapped onto it such that a radial force acts on a retention edge of the retention insert so that the retention edge is moved at least partially in the direction of a holding edge of the holding shell.

In this method, a screwdriver is preferably used as described above for fastening the abutment onto the jawbone, onto an implant which is implanted in the jawbone, onto a tooth stump or onto a neighboring tooth, such that the screwdriver is placed on the abutment in such a way that the acting surfaces of the acting section of the screwdriver are in contact with the acting surfaces of the body section of the abutment. Such a screwdriver enables efficient screw connection of the abutment.

Another further aspect of the present disclosure relates to a measurement device for measuring the gingival height of the top side of an implant that has been implanted in the jawbone, comprising an elongated measurement body, a profile support element and an adjusting device, such that the adjusting device is designed to place the measurement body on the top side of the implant and such that the profile support element is attached to the measurement body so that it is movable and the profile support element can be displaced along the measurement body. Such a measurement device makes it possible to determine the gingival height with respect to the implant, so that a suitable abutment and in particular an abutment of a suitable height can efficiently be selected. The measurement device is therefore placed by means of the control element on the top side of the implanted abutment. The profile support element is then displaced along the measurement body until it is in contact with the gingiva and/or the gingival profile. In this position, the height of the gingiva can then be determined easily, for example, by means of a scale applied to the measurement body.

The adjusting device is preferably arranged on a first longitudinal end of the measurement body. Furthermore, the adjusting device is preferably designed as an adjusting surface protruding beyond the measurement body from a longitudinal axis of the measurement body. Such an adjusting device permits simple and efficient positioning of the measurement device on the top side of the implant.

The measurement body is preferably designed to be cylindrical and in particular essentially a circular cylinder, which permits simple implementation of the measurement device and a simple design of the displaceable profile support elements.

The profile support element is preferably designed as a disk having a passage, such that the passage corresponds to a cross-sectional profile of the measurement body, and the measurement body extends through the passage. In the case of a circular cylindrical measurement body, the passage is designed to be circular. Such a profile support element permits a simple and expedient embodiment of the profile support element.

A stop is preferably arranged on a second longitudinal end of the measurement body with which displacement of the profile support element along the measurement body can be blocked. This makes it possible to prevent the profile support element from being removed from the measurement body, which permits simplified handling of the measurement device.

The measurement device also preferably has an implant-centering protrusion, which can be inserted into an opening in the implant. With such an implant-centering protrusion in the form of a truncated circular cone, the measurement device can easily be positioned as intended, which can permit efficient measurement of the height of the gingiva.

The measurement device preferably has a hand grip. With such a hand grip, the measurement device may be conveniently operated manually. The hand grip may be arranged in proximity to the second longitudinal end of the measurement body in particular.

Another additional aspect of the present disclosure relates to an arrangement, which comprises a measurement device as described above and a screwdriver as described above. The arrangement may also comprise an abutment as described above and/or a retention insert, as described above. In particular the arrangement may also comprise a plurality of abutments, which have gingival height sections of different heights designed with different lengths, for example.

BRIEF DESCRIPTION OF THE DRAWINGS

The invention is explained in greater detail below with reference to the accompanying drawings on the basis of exemplary embodiments, in which.

WAY(S) OF IMPLEMENTING THE INVENTION

Figure 1:
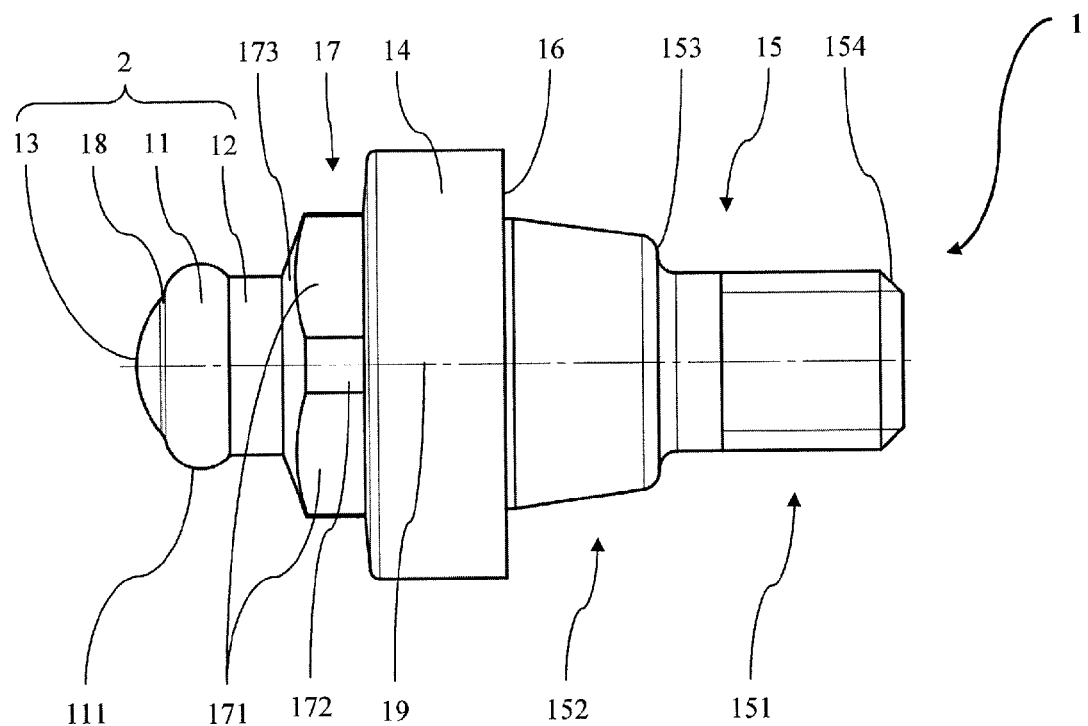
FIG. 1 shows a side view of a first exemplary embodiment of an abutment according to the invention.

Certain terms are used for practical reasons in the following description and are not to be understood as restrictive. The words "right," "left," "top" and "bottom" refer to directions in the drawings to which reference is being made. The terms "inwardly" and "outwardly" refer to directions into, toward or away from the geometric midpoint of the abutment and/or of the retention insert as well as the stated parts of same. The terminology includes the words mentioned explicitly above, derivations of the same and words of similar meanings.

Furthermore, the following applies to the entire following description. If a figure contains reference numerals for the sake of lack of ambiguity in the drawing, but these reference numerals are not mentioned in the text of the description directly associated therewith, then reference is made to their explanation in the description of the figures above. Furthermore, if reference numerals that are not contained in the respective figure are mentioned in the description text directly belonging to a figure, then reference is made to the preceding figures.

Figure 2:
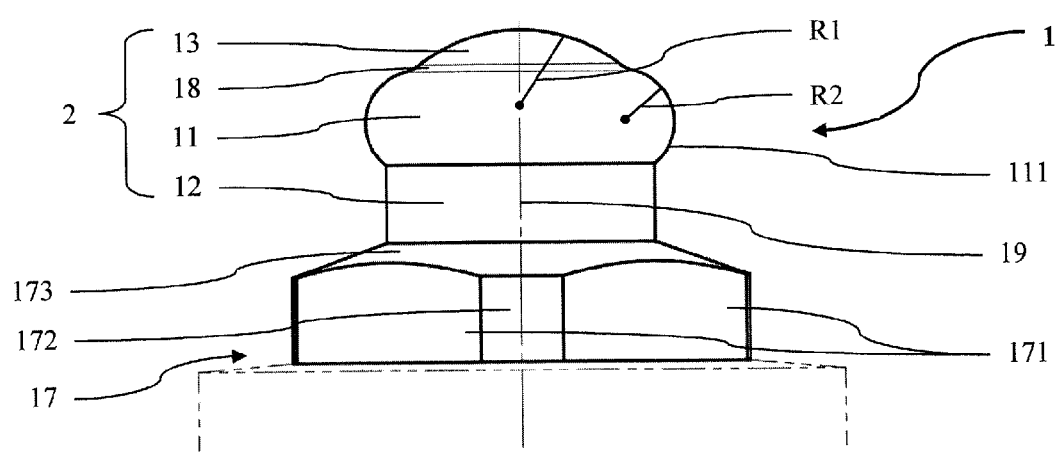
FIG. 2 shows an enlarged side view of the male piece of the abutment of FIG. 1.
Figure 3:
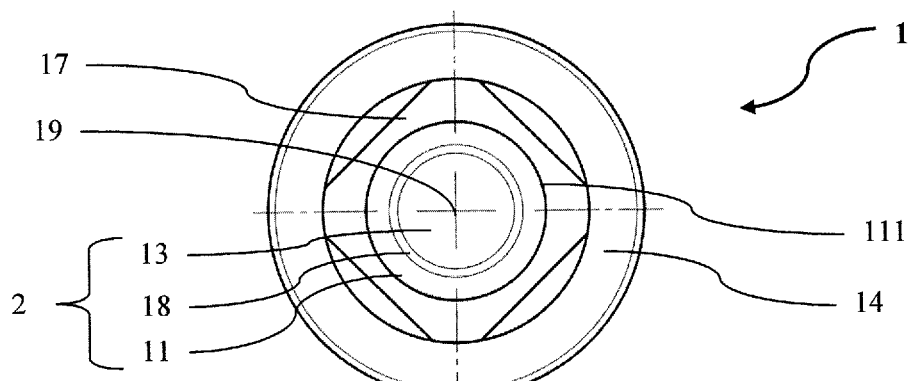
FIG. 3 shows a top view of the male piece of the abutment from FIG. 1.

FIGS. 1, 2 and 3 show a first exemplary embodiment of a one-piece abutment 1 having a central longitudinal axis 19, said abutment including a male piece 2 and a fastening structure having a screw section 15 which includes an intermediate section 152 without an outside thread and a threaded section 151 connected axially thereto and having an outside thread. The outside thread of the threaded section 151 is designed to correspond to the inside thread of the respective implant. At its longitudinal end, which faces away from the threaded section 151, the intermediate section 152 is connected to a circular cylindrical gingival height section 14. The intermediate section 152 is designed to taper from the gingival height section 14 to the threaded section 151. The gingival height section 14 protrudes beyond the first region of the intermediate section 151 outward from the longitudinal axis 19 of the abutment 1, i.e., in the distal direction, so that a planar surface 16 situated at a right angle to the longitudinal axis 19 forms a stop. Opposite the gingival height section 14, the intermediate section 152 develops axially into the threaded section 151 of the screw section 15 by way of an additional curved stop surface 153. The threaded section 151 ends in an end region 154, which tapers conically on its end facing away from the male piece 2.

On its end facing away from the screw section 15, the gingival height section 14 is connected axially to the male piece 2 of the abutment 1 by way of a wrench attachment section 17. The wrench attachment section 17 has a suitable shape for attaching a square wrench. In particular, the wrench attachment section 17 comprises four planar acting surfaces 171 arranged along the circumference of the wrench attachment section 17 and at a right angle to one another, two of these acting surfaces being joined to one another via a curved connecting surface 172. As the transition to the male piece 2, the wrench attachment section 17 has a conical transition region 173 which tapers from the acting surfaces 171 to the male piece 2.

The male piece 2 comprises a circular cylindrical body section 12, which is adjacent to the transitional region 173 of the wrench attachment section 17 and in turn passes over into a snap-on section 11 at its end facing away from the wrench attachment section 17. The snap-on section 11 has an exterior surface 111, which has a convex outward and/or distal curvature having a radius of curvature R2 from the longitudinal axis 19 of the abutment 1 outward along the longitudinal axis 19. The exterior surface 111 protrudes beyond the longitudinal axis of the abutment toward the outside, i.e., distally essentially completely protruding beyond the exterior surface of the body section 12. At its end facing away from the body section 12, the snap-on section 11 passes from a concave intermediate section 18 into a spherical segment-shaped head end 13 having a radius of curvature R1. The radius of curvature R1 of the head end 13 is approximately three times greater than the radius of curvature R2 of the exterior surface 111 of the snap-on section 11. The body section 12, the snap-on section 11, the intermediate section 18 and the head end 13 together form the male piece 2.

FIG. 3 shows the abutment 1 in a view from above, where it can be seen in particular that the four acting surfaces 171 of the wrench attachment section 17 are each arranged at a right angle to the neighboring acting surfaces 171 and are each connected by one of the curved connecting surfaces 172 to one of the neighboring acting surfaces 171. Thus the cross section of the wrench attachment section 17 describes a square such that the acting surfaces 171 each form right angles to one another and the longitudinal axial 19 of the abutment 1 forms the midpoint of the hexagon. The wrench attachment section 17 protrudes beyond the male piece 2 from the longitudinal axis 19 outward, i.e., in the distal direction.

The abutment 1 is manufactured completely of titanium, whereby, as an alternative to this, another biocompatible material is also possible. The diameter of the largest cross section of the snap-on section 11 at a right angle to the longitudinal axis 19 has a length of 2.1 mm to 2.7 mm and in particular 2.3 mm. The largest diameter of the cross section of the wrench attachment section 17 at a right angle to the longitudinal axis 19 has a length of 3.1 mm to 3.7 mm and in particular 3.4 mm. The distance between the two parallel acting surfaces 171 is between 2.5 mm and 3.1 mm and in particular 2.8 mm. The male piece 2 has a total height of between 3 mm and 3.8 mm and in particular 3.4 mm. The radius of curvature R1 of the head end 13 in the shape of a spherical segment has a length of between 1 mm and 1.4 mm and in particular 1.2 mm. The radius of curvature R2 of the exterior surface 111 of the snap-on section 11 has a length of between 0.3 mm and 0.5 mm, and in particular 0.4 mm.

Figure 4:
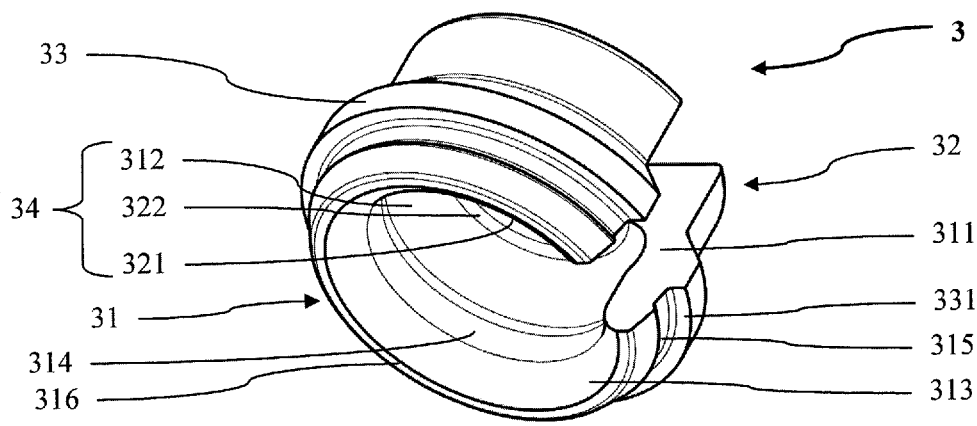
FIG. 4 shows a perspective view of a first exemplary embodiment of a retention insert according to the invention that fits with the abutment from FIG. 1.
Figure 5:
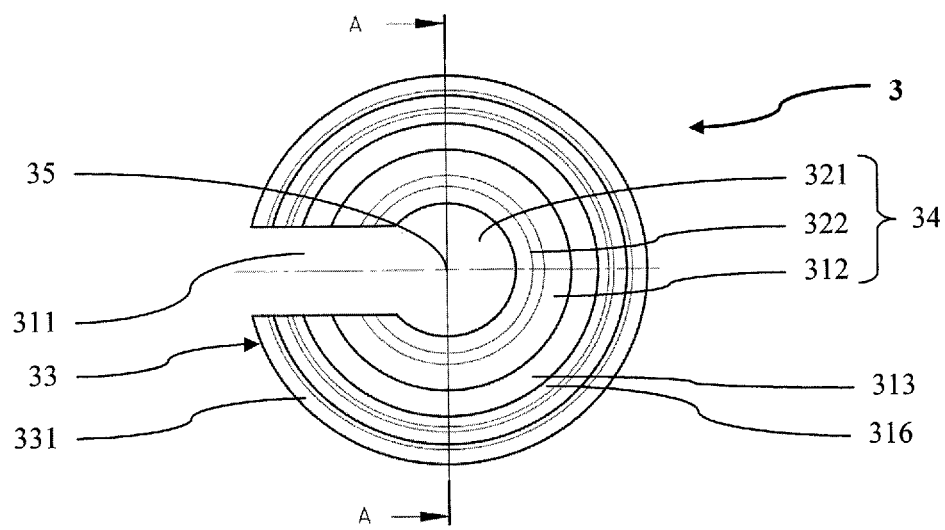
FIG. 5 shows a view of the retention insert from FIG. 4 as seen from underneath.
Figure 6:
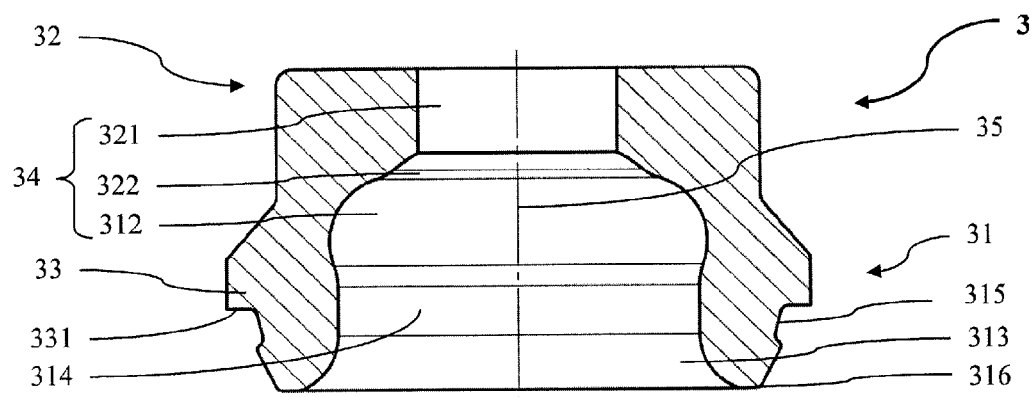
FIG. 6 shows a cross-sectional view along line A-A of the retention insert from FIG. 5.

FIG. 4 shows a perspective view of a first exemplary embodiment of a retention insert 3 according to the invention that fits the male piece 2 of the abutment 1 of the preceding figures. FIG. 5 shows a view from below of the same retention insert 3, and FIG. 6 shows a sectional view of the same retention insert 3. The essentially pot-shaped retention insert 3 with a central axis 35 comprises an end side 32 essentially in the form of a circular disk having a central circular opening 321 as the first region and an essentially ring-shaped retention edge 31 protruding away from that at an angle on the circumference. The retention edge 31 is interrupted by a vertical slot 311, which extends up to the opening 321 of the retention edge 32. The slot 311 is arranged at a right angle to the end 32 and is designed to be straight.

The retention edge 31 has an exterior surface and an interior surface opposite the exterior surface, such that the interior surface is designed to be rounded outward toward the open end of the retention insert 3, i.e., toward the end of the retention insert 3 facing away from the end side 32 and thus has a corresponding curved section 313. The interior surface of the retention edge 31 here has a first upper concave region 312 that is curved inward with a positive radius of curvature, developing downward into an extension region 314 by way of a slightly convex section. The extension region 314 has a planar inside, which is essentially in the form of the inside of a ring. Toward the top, the first region 312 of the retention edge 31 in turn develops, by way of a section with a slight convex curvature, into a third region 322 of the end side 32 with an interior surface tapering conically toward the top. The third region 322 develops toward the top into the opening 321 of the end side 32. The first region 311 of the retention edge 31 together with the third region 322 and the opening 321 of the end side 32 forms a frame 34.

On the end of the retention edge 31 facing away from the end side 32, the outwardly curved section 313 passes over into a planar section 316 which forms the end of the retention insert 3 facing away from the end side 32. In application of the retention insert 3, the planar section 316 may correspond to the apical end of the retention insert 3.

Approximately at the center of the retention edge 31, a bar-shaped protrusion 33 and/or a beam that extends radially from the exterior surface of the retention edge 31 and extends over the entire circumference of the retention edge 31 is designed approximately at the center of the retention edge 31. The protrusion 33 includes a planar radial exterior side, a planar top side designed at a right angle to the former, facing the end side 32, and a planar bottom side opposite the top side and facing away from the inside 32, defining a protruding support surface 331. As can be seen well in FIG. 5, the protrusion 33 extends radially outward beyond the remainder of the retention insert 3.

An engagement notch 315 is formed near the protrusion 33 on the exterior surface in the direction of the end of the retention edge 31 facing away from the end side 32. The retention insert 3 can be secured by means of the engagement notch 315 by using a suitable assembly tool, as described in WO 2011/027229 A2, for example. The retention insert 3 can therefore be assembled and manipulated in the preferred manner.

The retention insert 1 is made completely of polyether ether ketone, but some other biocompatible polymer or non-polymer material is also possible as an alternative. The radius of curvature of the first region 312 of the frame 34 is designed according to the radius of curvature R1 of the exterior surface 111 of the snap-on section 11 of the male piece 2 and has a length between 0.3 mm and 0.5 mm and in particular 0.4 mm. The opening 321 in the frame 34 has a diameter between 1.5 mm and 1.7 mm and in particular 1.6 mm. The extension region 314 has a thickness, i.e., height, between 0.1 mm and 0.5 mm or 0.2 mm to 0.4 mm and in particular 0.3 mm.

In use of the abutment 1 together with the retention insert 3, the abutment 1 and/or in most cases several such abutments 1 are permanently connected to the jawbone via an implant that has already been implanted. In parallel with that, a prosthetic construction is prepared, so that openings and/or blind holes are provided in the site(s) of the prosthetic construction where it should be possible to connect the prosthetic construction to the abutment(s) 1 by means of one or more female pieces. Then the retention inserts 3 and fitting female housings are placed on the male pieces 2 of the abutments 1. The geometry of the male pieces 2 in particular with their concave intermediate sections 18 and the geometry of the retention inserts 3 in particular with their frames 34 allow the retention inserts 3 to be held adequately on the male pieces 2 in predetermined alignment and position and make it possible to prevent an unintentional tilting of the retention inserts 3 on the male pieces 2 or at least allow it to be restricted. The male pieces 2 thus have a self-centering function on the respective female piece and/or its retention insert 3. In particular the respective retention insert 3 is prestressed in the event of tilting, due to the geometry of the male pieces 2, so that it is automatically moved back into the above-mentioned preferred predetermined alignment and/or position as soon as it has the required clearance to do so. In this preferred predetermined alignment and/or position, the male pieces 2 may then be arranged in the openings in the prosthetic construction and the female housings may be permanently connected to the prosthetic construction, for example, by means of fully polymerizing the openings of the prosthetic construction.

In daily use of the abutments 1 and the retention inserts 3, the geometry of the male pieces 2 of the abutments 1 and the frames 34 of the retention inserts 3 allows a relatively great tilting of the female pieces on the male pieces 2 to be possible, and in particular the respective lengthening sections 314 of the retention inserts 3 provide additional clearance for such a tilting movement.

The spherical segment shape of the male pieces 2 of the abutments 1 makes it possible for the prosthetic construction to be positioned accurately and easily in a relatively gentle manner when the female pieces are mounted on the prosthetic construction, so that comfortable insertion of the prosthetic construction is possible and damage to the female pieces due to corners or edges of the head end, for example, can be prevented. Furthermore, the design of the male pieces 2 means that their head ends 13 are arranged relatively far apart axially from the sides of the snap-on sections 11 that are opposite the body sections 12. The head ends 13 of the male piece 2 are therefore at a higher level in comparison with their snap-on sections 11, i.e., they extend farther into the patient's mouth. The head ends 13 can be raised further from the gingiva in comparison with the snap-on sections 11 in this way, so that the male pieces 2 can be localized relatively easily and unambiguously before insertion of the prosthetic construction.

Figure 7:
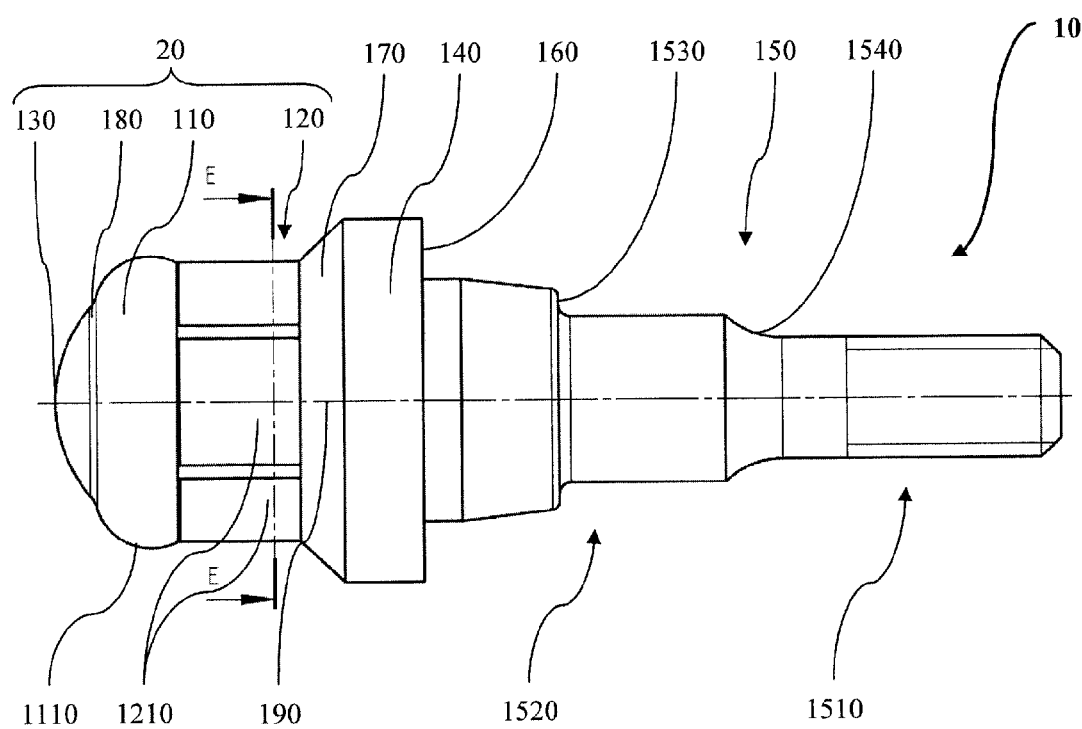
FIG. 7 shows a side view of a second exemplary embodiment of an abutment according to the invention.
Figure 8:
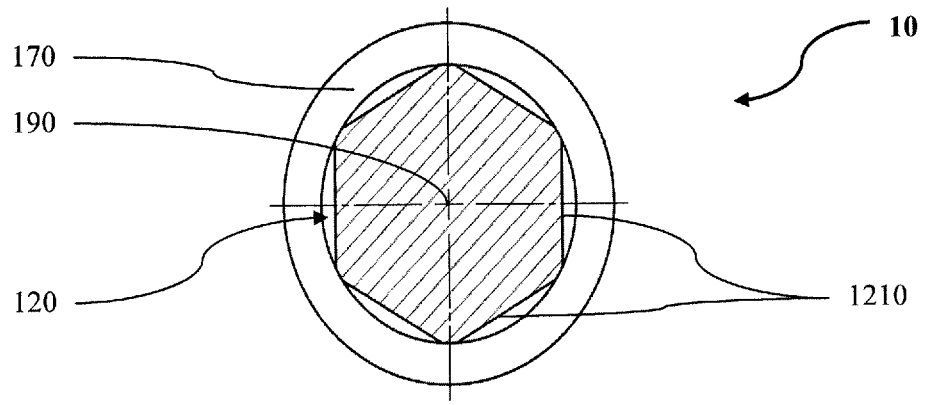
FIG. 8 shows a cross-sectional view along line E-E of the male piece of the abutment from FIG. 7.
Figure 9:
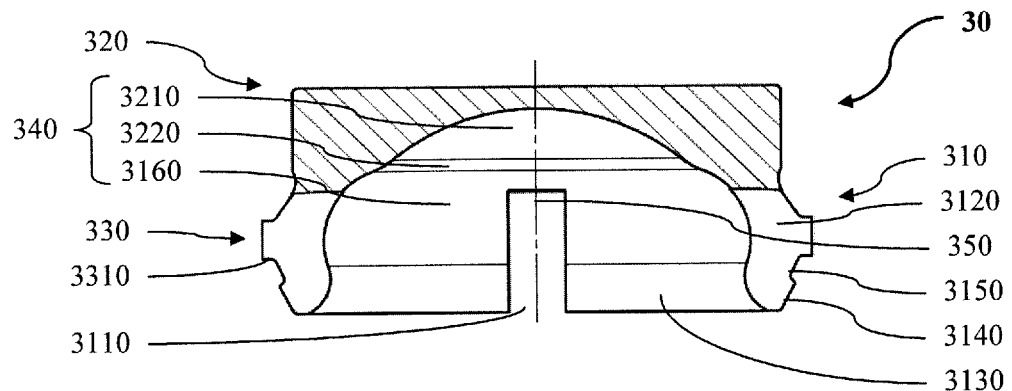
FIG. 9 shows a cross-sectional view of a second exemplary embodiment of a retention insert according to the invention that fits with the abutments of FIG. 7.

FIGS. 7 and 8 show a second exemplary embodiment of a one-piece abutment 10 which, like the abutment in FIGS. 1, 2 and 3, is designed with a central longitudinal axis 190, a male piece 20, a gingival height section 140 and a screw section 150. The screw section 150 comprises an intermediate section 1520 with a first stop surface 1530 and a second stop surface 1540 and a threaded section 1510. Between the screw section 150 and the gingival height section 140 a planar surface 160 situated at a right angle to the longitudinal axis 190 is formed as a stop.

The male piece 20 of the abutment 10 comprises a hexagonal cylindrical body section 120, which is axially adjacent to a transitional section 170 in the form of a truncated circular cone, this body section in turn developing into a snap-on section 110 at its end facing away from the transitional section 170. The exterior surface of the body section 120 is formed by six rectangular acting surfaces 1210 standing at a 60° angle to one another.

The snap-on section 110 has an exterior surface 1110, which has a convex outward curvature, i.e., distally from the longitudinal axis 190 of the abutment 10 outward along the longitudinal axis 190. The exterior surface 1110 protrudes from the longitudinal axis 190 of the abutment 10 outward, i.e., in the distal direction essentially completely beyond the exterior surface of the body section 120. The snap-on section 110 develops into a head end 130 in the form of a spherical segment on its end facing away from the body section 120 by means of an intermediate section 180 having an exterior surface with a concave curvature.

The abutment 10 is made completely of titanium, but as an alternative to this, some other suitable biocompatible material is also possible. The snap-on section 110 has a larger diameter of the largest cross section situated at a right angle to the longitudinal axis 190, than the snap-on section 11 of the abutment 1 from FIGS. 1, 2 and 3, and is designed with dimensions approximately like the known similar push-button connections traditionally used with snap-on sections. In other words, it is within a range of approximately 3.8 mm to approximately 4 mm and in particular approximately 3.9 mm.

Figure 10:
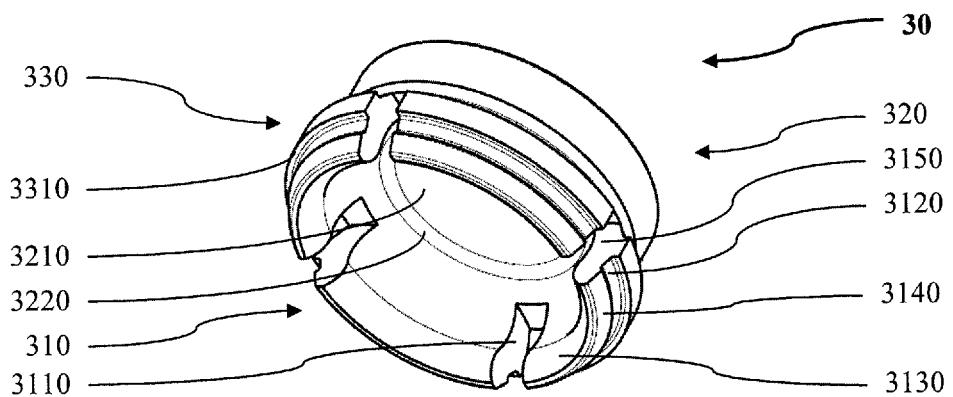
FIG. 10 shows a perspective view of the retention insert from FIG. 9.
Figure 11:
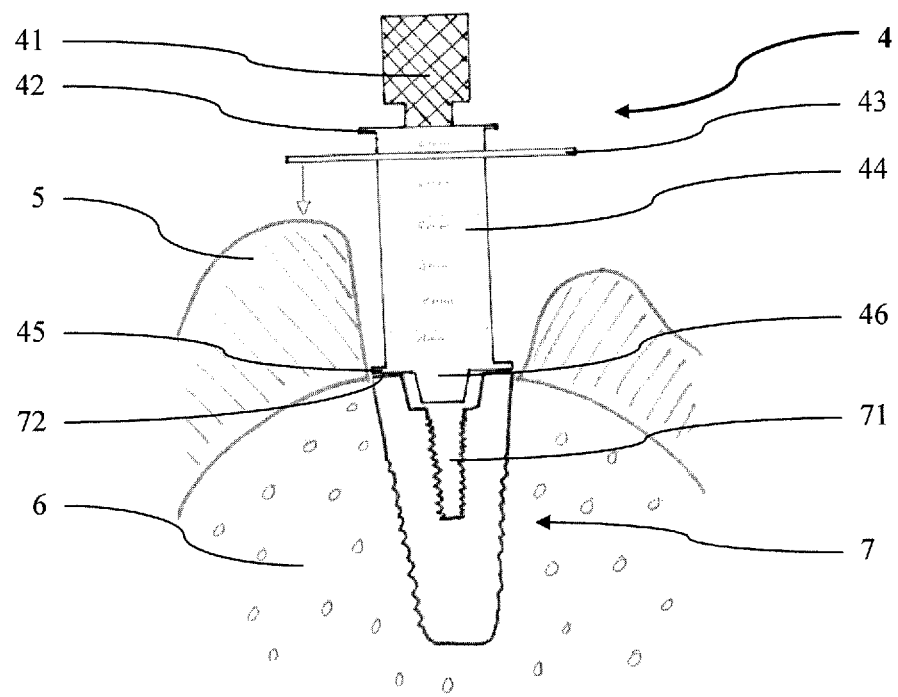
FIG. 11 shows a partially sectional side view of one exemplary embodiment of a measurement device.

FIGS. 10 and 11 show a retention insert 30 according to the invention which is inclined for use with the abutment 10 from FIGS. 7 and 8 and has a central axis 350. The retention insert 30 comprises an end side 320 and a retention edge 310 with an exterior surface 3140, four recesses 3110 and lamellar section 3120. In addition, the retention insert 30 has a bar-shaped protrusion 330 with a planar radial exterior side, a planar top side designed at a right angle to the former and a planar bottom side, which is also designed at a right angle thereto and describes a protruding support surface 3310. A suspension groove 3150 is also designed beneath the protrusion 330.

The lamellar sections 3120 have an interior surface 3160 as the first region of a frame 340, which describes an interior surface of the retention edge 310 opposite the exterior surface 3140. The interior surfaces 3160 of the lamellar sections 3120 as well as a concave intermediate section 3220 as the third region of the frame 340 and an interior surface 3210 in the form of a spherical segment of the end side 320 as a second region of the frame 340 are designed together corresponding to the exterior surface of the snap-on section 110, the support section 180 and the end side 130, i.e., of the male piece 20 of the abutment 10. Furthermore, the interior surfaces 3160 of the lamellar sections 3120 are designed with an outward rounding toward the open end of the retention insert 30, i.e., toward the end of the retention insert 30 facing away from the end side 320 and thus have a corresponding curved section 3130.

During operation, the retention insert 30 may advantageously be used like the retention inserts described in WO 2011/027229 A2 together with a corresponding holding shell for connecting the prosthetic construction to the abutment 10. Furthermore, the intermediate section 3220 of the retention insert 30 permits the retention insert 30 to be used as intended with a traditional abutment, which has an opening on its head end, as described in WO 2010/025034 A1, for example.

FIG. 11 shows a measurement device 4 for measuring a gingival height of a top side 72 of an implant 7 implanted in a jawbone 6. The implant 7 is implanted in the jawbone 6, so that it is approximately flush and has a blind hole 71 extending into the interior of the implant on its top side 72. The blind hole 72 partially has an interior thread into which an exterior thread of an abutment can be screwed.

The measurement device 4 comprises a circular cylindrical measurement body 44 with a scale on its exterior surface which passes over into a circular disk-shaped adjusting surface 45 as adjusting device on its first lower longitudinal end. The adjusting surface 45 protrudes outward beyond the measurement body 44 from a central longitudinal axis of the measurement body 44. On its side facing away from the measurement body 44, an implant-centering protrusion 46 in the form of a truncated cone is provided on the adjusting surface 45.

The measurement device 4 additionally comprises a disk 43 which is adjustable in height as the profile-supporting element having a circular passage through which the measurement body 44 extends. The disk 43 is movable and/or displaceable longitudinally along the measurement body 44. On an upper second longitudinal end, the measurement body 44 has a disk stop 42, which blocks and limits the movement of the disk 43 upward so that the disk 43 cannot be moved away from the measurement body 44.

Above the disk stop 42, i.e., on a side of the disk stop 42 facing away from the measurement body 44 a hand grip 41 is formed on which the measurement device 4 can be held manually for simple handling.

During operation, the user holds the measurement device on the hand grip 41 and inserts it together with the implant-centering protrusion 46 into the blind hole 71 of the implant until, as shown in FIG. 12, the adjusting surface 45 rests on the top side 72 of the implant 7. As indicated by the arrow in FIG. 12, the disk 43 is then displaced and/or lowered along the measurement body 44 as far as the profile of a gingiva 5 attached to the jawbone 6. In this position, in which the disk 43 rests on the gingival profile, the gingival height is read by means of the scale on the measurement body 44. For example, the scale may be designed for reading of gingival heights in a range from approximately 0 mm to approximately 6 mm. The gingival height ascertained in this way may be used, for example, to select an abutment of suitable dimensions and/or a suitable abutment height.

Although the invention is illustrated and described in detail with reference to the figures and the respective description, these illustrations and this detailed description are to be understood as being illustrative and exemplary but not as restricting the invention in any way. It is self-evident that experts in the field will be able to make modifications and changes without going beyond the scope and the spirit of the following claims. In particular the invention also includes specific embodiments with the respective combination of features mentioned or presented above or below for various embodiments.

The invention also comprises individual features in the figures even if they are shown there only in conjunction with other features and/or they are not mentioned above or below. The alternatives of specific embodiments and individual alternatives that are illustrated in the figures and described in the description and whose features are excluded from the subject matter of the invention and/or from the disclosed subject matters may also be excluded. The disclosure comprises specific embodiments, which comprise exclusively the features described in the claims and/or in the exemplary embodiments as well as those comprising other additional features.

In addition, the term "comprise" and derivations thereof do not preclude other elements or steps. Likewise, the indefinite article "a" and/or "an" and derivations thereof also do not preclude a plurality. The functions of multiple features included in the claims may be satisfied by a unit and/or a step. The mere fact that certain dimensions are cited in different dependent claims does not mean that a combination of these dimensions cannot be used to advantage. The terms "essentially," "substantially," "approximately," "about" and the like in conjunction with a property and/or a value also define precisely the property and/or precisely the value in particular. The terms "about" and "approximately" in conjunction with a given numerical value or numerical range may relate to a value and/or a range which is within 20%, within 10%, within 5% or within 2% of the given value and/or range. All the reference numerals in the claims are to be understood as not restricting the scope of the claims.

The present disclosure also consists of the following exemplary embodiments of various subject matters:

Exemplary embodiment 1 is an abutment for connecting a dental prosthetic construction to a jawbone, said abutment being designed with a fastening structure by means of which said abutment can be fastened onto the jawbone, onto an implant that has been implanted in the jawbone, onto a tooth stump or onto a neighboring tooth, and comprising: a body section having an exterior surface which corresponds essentially to a lateral surface of a cylinder, wherein the central axis of the cylinder defines a longitudinal axis of the abutment; a snap-on section that is offset axially with respect to the longitudinal axis of the abutment toward the body section and comprises an exterior surface, which has a convex curvature and protrudes outward beyond the exterior surface of the body section from the longitudinal axis of the abutment; and a head end which ends the abutment axially with respect to its longitudinal axis, such that the snap-on section is arranged closer to the head end than is the body section, where the cylinder of the lateral surface which corresponds essentially to the exterior surface of the body section, has a cross section essentially in the form of a polygon perpendicular to the longitudinal axis of the abutment so that a plurality of essentially rectangular acting surfaces are designed on the exterior surface of the body section.

Exemplary embodiment 2 is the abutment from exemplary embodiment 1 in which the cross section of the cylinder of the lateral surface which corresponds essentially to the exterior surface of the body section, has essentially the shape of a hexagon or an octagon.

Exemplary embodiment 3 is the abutment from exemplary embodiment 1 or 2, in which the head end of the abutment is designed essentially with a completely convex curvature and is closed.

Exemplary embodiment 4 is the abutment of exemplary embodiment 3 in which the head end of the abutment corresponds essentially to a segment of a spherical surface.

Exemplary embodiment 5 is the abutment of exemplary embodiment 3 or 4, in which a support section with an exterior surface having a concave curvature is arranged between the exterior surface of the snap-on end having a convex curvature and the head end which has a convex curvature.

Exemplary embodiment 6 is the abutment from one of the preceding exemplary embodiments, in which the fastening structure has a screw section which extends axially away from the head end and comprises at least partially an outside thread.

Exemplary embodiment 7 is the abutment from one of the preceding exemplary embodiments, comprising an essentially cylindrical gingival height section that protrudes beyond the body section outward from the longitudinal axis of the abutment, where the body section is arranged closer to the head end of the abutment than is the gingival height section.

Exemplary embodiment 8 is the abutment from exemplary embodiments 6 and 7, in which the gingival height section protrudes beyond the screw section of the fastening structure outward from the longitudinal axis of the abutment, a stop being formed between the gingival height section and the screw section of the fastening structure.

Exemplary embodiment 9 is the abutment from exemplary embodiment 8, in which the stop between the body section and the screw section of the fastening structure is designed as an essentially planar surface arranged at a right angle to the longitudinal axis.

Exemplary embodiment 10 is the abutment from one of the exemplary embodiments 6 to 9, in which the screw section of the fastening structure comprises an intermediate section without an outside thread and a threaded section with an outside thread.

Exemplary embodiment 11 the abutment from exemplary embodiment 10, in which the intermediate section of the screw section of the fastening structure tapers from the gingival height section to the threaded section.

Exemplary embodiment 12 is the abutment from exemplary embodiment 11, in which the intermediate section has at least one step.

Exemplary embodiment 13 is a connecting device for connecting a dental prosthetic construction to a jawbone, which comprises an abutment according to one of the exemplary embodiments 1 through 12 and a retention insert for snapping onto the snap-on section of the abutment, wherein the retention insert has an end side and an essentially ring-shaped retention edge protruding away from that, such that the end side and the essentially ring-shaped retention edge protruding away from it together form a receptacle having an interior surface, which is designed to correspond to the exterior surface of the abutment from the snap-on section to the head end.

Exemplary embodiment 14 is a retention insert for snapping onto a snap-on section of an abutment according to one of the exemplary embodiments 1 through 12, having an end side and an essentially ring-shaped retention edge protruding away from it such that the end side and the essentially ring-shaped retention edge protruding away from it form a receptacle having an interior surface, comprising a first concave region, which is designed to correspond to the exterior surface of the snap-on section of the abutment, a second concave region, which is designed to receive the head end of the abutment, and a convex region, which is designed between the first concave region and the second concave region.

Exemplary embodiment 15 is a method for connecting a dental prosthetic construction to a jawbone, comprising:
fastening an abutment according to one of the exemplary embodiments 1 through 12, wherein the abutment has a fastening structure by means of which the abutment is attached to the jawbone, to an implant that has been implanted in the jawbone, to a tooth stump or to a neighboring tooth;
secure mounting of a holding shell on the prosthetic construction;
axially impressing a retention insert according to exemplary embodiment 14 into the holding shell until the retention insert is arranged in the holding shell;
arranging the prosthetic construction on the abutment so that a head end of the abutment is in contact with the retention insert; and
pressing the prosthetic construction onto the abutment so that the retention insert is pressed axially over a snap-on section of the abutment and is snapped onto it such that a radial force acts on a retention edge of the retention insert so that the retention edge is moved at least partially in the direction of a holding edge of the holding shell.

Exemplary embodiment 16 is the method according to exemplary embodiment 15, in which a screwdriver is used for fastening the abutment onto the jawbone, onto an implant that has been implanted in the jawbone, onto a tooth stump or onto a neighboring tooth, such that the screwdriver is placed on the abutment so that the acting surfaces of an acting section of the screwdriver are in contact with the acting surfaces of the body section of the abutment.

Exemplary embodiment 17 is a measurement device for measuring the height of the gingiva from the top side of an implant being implanted in a jawbone, comprising an elongated measurement body, a profile support element and an adjusting device, wherein the adjusting device is designed to position the measurement body on the top side of the implant and wherein the profile support element is movably attached to the measurement body so that the profile support element is displacable along the measurement body.

Exemplary embodiment 18 is the measurement device according to exemplary embodiment 17, in which the adjusting device is arranged on a first longitudinal end of the measurement body.

Exemplary embodiment 19 is the measurement device according to exemplary embodiment 17 or 18 in which the adjusting device is designed as an adjusting surface which protrudes beyond the measurement body from a longitudinal axis of the measurement body.

Exemplary embodiment 20 is the measurement device according to any one of the exemplary embodiments 17 through 19 in which the measurement body is designed to be cylindrical or is cylindrical.

Exemplary embodiment 21 is the measurement device according to any one of the exemplary embodiments 17 through 20 in which the profile support element is designed as a disk having a passage such that the passage corresponds to a cross-sectional profile of the measurement body and the measurement body protrudes through the passage.

Exemplary embodiment 22 is the measurement device according to any one of the exemplary embodiments 17 through 21 in which a stop is arranged on a second longitudinal end of the measurement body with which the displacement of the profile support element along the measurement body can be blocked.

Exemplary embodiment 23 is the measurement device according to any one of the exemplary embodiments 17 through 22 which has an implant-centering protrusion, which can be inserted into an opening in the implant.

Exemplary embodiment 24 is the measurement device according to any one of the exemplary embodiments 17 through 23, which has a holding grip.

The invention claimed is:

1. A male piece for reversible and detachable connection of a dental prosthetic construction to a jawbone, said male piece being designed with a fastening structure by means of which the male piece can be fastened onto the jawbone, onto an implant that has been implanted in the jawbone, onto a tooth stump or onto a neighboring tooth, comprising:
a body section having an exterior surface corresponding to a lateral surface of a cylinder, wherein the central axis of the cylinder defines a longitudinal axis of the male piece;
a snap-on section, which is axially offset with respect to the longitudinal axis of the male piece relative to the body section, said snap-on section comprising an exterior surface with a convex curvature along the longitudinal axis, which protrudes outward beyond the exterior surface of the body section from the longitudinal axis of the male piece; and
a head end which closes the male piece axially with respect to its longitudinal axis,
wherein the snap-on section is arranged closer to the head end than is the body section, and
wherein a concave intermediate section is arranged between the head end and the convexly curved exterior surface of the snap-on section, wherein
the head end of the male piece completely is convexdly curved and closed,
the head end of the male piece corresponds to a segment of a spherical surface, and
the segment of the spherical surface of the head end has a first radius of curvature and the convexly curved exterior surface of the snap-on section has a second radius of curvature, wherein the first radius of curvature is greater than the second radius of curvature.

2. The male piece according to claim 1, wherein the intermediate section of the male piece has a concavely curved exterior surface.

3. The male piece according to claim 1, in which the first radius of curvature is approximately two to approximately four times larger than the second radius of curvature and in particular is approximately three times larger.

4. An abutment for connecting a dental prosthetic construction to a jawbone, comprising:
a male piece according to claim 1; and
a fastening structure, by means of which the abutment can be fastened onto the jawbone or onto an implant that is implanted in the jawbone.

5. The abutment according to claim 4, in which the fastening structure has a screw section extending away from the head end of the male piece, an outside thread being formed at least partially on said screw section.

6. The abutment according to claim 5, in which the fastening structure comprises a wrench attachment section arranged between the screw section and the male piece.

7. A retention insert for snap-on connection of a snap-on section of a male piece according to claim 1, which has an end side and an at least partially ring-shaped retention edge protruding away from same, wherein the end side and the retention edge protruding away from it form a frame which comprises a first concave region corresponding to the exterior surface of the snap-on section of the male piece, a second region designed to receive the head end of the male piece and a third region between the first region and the second region.

8. The retention insert according to claim 7, wherein the second region of the frame is designed as a continuous opening in the end side.

9. The retention insert according to claim 7, wherein the third region of the frame has a conical interior surface which tapers from the first region of the frame to the second region of the frame.

10. The retention insert according to claim 7, wherein the retention edge has an extension region, which is connected to the first region of the frame opposite the third region of the frame.

11. The retention insert according to claim 10, comprising a central longitudinal axis, wherein the diameter of a maximum cross section of the first region arranged perpendicular to the central longitudinal axis has a length between approximately six and approximately fourteen, preferably between approximately eight and approximately twelve and in particular approximately ten times the thickness of the extension region.

12. A connecting device comprising:
a male piece according to claim 1 and a retention insert which has an end side and an at least partially ring-shaped retention edge protruding away from same, wherein the end side and the retention edge protruding away from it form a frame which comprises a first concave region corresponding to the exterior surface of the snap-on section of the male piece, a second region designed to receive the head end of the male piece and a third region between the first region and the second region, wherein the third region of the retention insert is arranged at least partially at a distance from the intermediate section of the male piece when the retention insert is snapped onto the male piece and no outer force is acting on the retention insert and/or the male piece.

* * * * *